United States Patent
Aoki et al.

(10) Patent No.: US 12,416,736 B2
(45) Date of Patent: Sep. 16, 2025

(54) RADIOGRAPHIC DEVICE

(71) Applicants: NATIONAL UNIVERSITY CORPORATION SHIZUOKA UNIVERSITY, Shizuoka (JP); ANSeeN Inc., Shizuoka (JP)

(72) Inventors: Toru Aoki, Hamamatsu (JP); Katsuyuki Takagi, Hamamatsu (JP); Akifumi Koike, Hamamatsu (JP)

(73) Assignees: NATIONAL UNIVERSITY CORPORATION SHIZUOKA UNIVERSITY (JP); ANSeeN Inc. (JP)

( * ) Notice: Subject to any disclaimer, the term of this patent is extended or adjusted under 35 U.S.C. 154(b) by 168 days.

(21) Appl. No.: 18/252,128

(22) PCT Filed: Nov. 13, 2020

(86) PCT No.: PCT/JP2020/042488
§ 371 (c)(1),
(2) Date: May 8, 2023

(87) PCT Pub. No.: WO2022/102095
PCT Pub. Date: May 19, 2022

(65) Prior Publication Data
US 2024/0004092 A1    Jan. 4, 2024

(51) Int. Cl.
*G01T 1/24*    (2006.01)
(52) U.S. Cl.
CPC .................... *G01T 1/247* (2013.01)
(58) Field of Classification Search
None
See application file for complete search history.

(56) References Cited

U.S. PATENT DOCUMENTS

2014/0226166 A1\* 8/2014 Kumar .................. H04N 25/78
356/601

FOREIGN PATENT DOCUMENTS

| CN | 108618792 A | 10/2018 |
|---|---|---|
| CN | 111919140 A | 11/2020 |

(Continued)

OTHER PUBLICATIONS

International Search Report mailed Jan. 26, 2021 in corresponding PCT International Application No. PCT/JP2020/042488.

(Continued)

*Primary Examiner* — Edwin C Gunberg
(74) *Attorney, Agent, or Firm* — OSTROLENK FABER LLP (57) ABSTRACT

A radiation imaging apparatus includes a plurality of pixels configured to generate an electric charge corresponding to energy or the number of particles of incident radiation, a plurality of signal processing parts respectively connected to the plurality of pixels and configured to generate a digital value based on the electric charge provided by each of the pixels, and a circuit board in which a radiation detector including the plurality of pixels and the plurality of signal processing parts is disposed in a two-dimensional manner. Each of the plurality of signal processing parts includes a signal conversion part configured to convert an analog value based on the electric charge into the digital value, and a clock signal generation part configured to provide a clock signal for generating a digital value to the signal conversion part.

4 Claims, 6 Drawing Sheets

(56) References Cited

FOREIGN PATENT DOCUMENTS

| | | |
|---|---|---|
| JP | S59-137874 A | 8/1984 |
| JP | 2010-021151 A | 1/2010 |
| JP | 2011-085479 A | 4/2011 |
| JP | 2012-032322 A | 2/2012 |
| JP | 2017-096798 A | 6/2017 |
| JP | 2020-507753 A | 3/2020 |
| WO | WO 2018/144127 A1 | 8/2018 |
| WO | WO 2020/077217 A1 | 4/2020 |

OTHER PUBLICATIONS

English translation of the International Preliminary Report on Patentability (IPRP) (Chapter 1 or II of the PCT Treaty) mailed May 25, 2023 with a Notification from the International Bureau (Form PCT/IB/338) issued in corresponding International Application No. PCT/JP2020/042488.

* cited by examiner

RADIOGRAPHIC DEVICE

CROSS-REFERENCE TO RELATED APPLICATION

The present application is a U.S. national stage application of PCT/JP2020/042488, filed Nov. 13, 2020, which is incorporated by this reference.

TECHNICAL FIELD

The present invention relates to a radiation imaging apparatus.

BACKGROUND ART

A technology for detecting radiation has been developed. The radiation detection technology is expected to be applied to the medical field, industrial field, security field, and the like. As an apparatus for detecting radiation, there is a radiation imaging apparatus for obtaining a radiation image. The radiation imaging apparatus outputs image data that indicates a state of incident radiation. To generate the image data, for example, signal processing such as converting an analog signal into a digital signal is performed. The signal processing is performed by providing a clock signal for driving an electronic circuit to the electronic circuit that exhibits a desired function. Patent Literature 1 and Patent Literature 2 disclose apparatuses for detecting X-rays or radiation. Further, Patent Literature 1 and Patent Literature 2 show that the apparatuses operate in response to a clock.

CITATION LIST

Patent Literature

[Patent Literature 1] Japanese Unexamined Patent Publication No. 2020-507753
[Patent Literature 2] PCT International Publication No. WO2020-077217

SUMMARY OF INVENTION

Technical Problem

In the technical field of radiation imaging apparatuses, it is desired to increase an area of an effective pixel region. The expansion of the effective pixel region is accompanied by an increase in the number of pixels. As the number of pixels increases, power consumption also tends to increase.

An object of the present invention is to provide a radiation imaging apparatus capable of curbing increase in power consumption.

Solution to Problem

A radiation imaging apparatus according to an embodiment of the present invention includes a plurality of pixels configured to generate electric charge corresponding to energy or the number of particles of incident radiation, a plurality of signal processing parts respectively connected to the plurality of pixels and configured to generate a digital value based on the electric charge provided by each of the pixels, and a circuit board in which a radiation detector including the plurality of pixels and the plurality of signal processing parts is disposed in a two-dimensional manner. Each of the plurality of signal processing parts includes a signal conversion part configured to convert an analog value based on the electric charge into the digital value, and a clock signal generation part configured to provide a clock signal for generating a digital value to the signal conversion part.

In the radiation imaging apparatus, the signal processing part is provided for each of the pixels. The signal processing part includes the signal conversion part and the clock signal generation part. That is, in the radiation imaging apparatus, the clock signal generation part is provided for each of the pixels. With such a configuration, it is possible to drive only the signal conversion part corresponding to the pixel on which the radiation is incident and not to drive the signal conversion part corresponding to a pixel on which radiation is not incident. Therefore, even when the number of pixels is increased, the signal conversion parts which do not need to be operated are not operated, and thus increase in power consumption can be curbed.

The clock signal generation part may start an operation of providing the clock signal to the signal conversion part triggered by generation of the electric charge due to incidence of the radiation on the pixels. With such a configuration, the signal conversion part can be operated each time radiation is incident.

The radiation imaging apparatus according to the embodiment of the present invention may further include a transmission signal generation part configured to provide a transmission signal for outputting the digital value from the signal processing part to the circuit board to each of the plurality of signal processing parts, and a wiring unit configured to transmit the transmission signal to the signal processing part. With such a configuration, the output operations of the plurality of signal processing parts can be synchronized.

Advantageous Effects of Invention

According to the present invention, there is provided a radiation imaging apparatus capable of suppressing an increase in power consumption.

DESCRIPTION OF EMBODIMENTS

Figure 1:
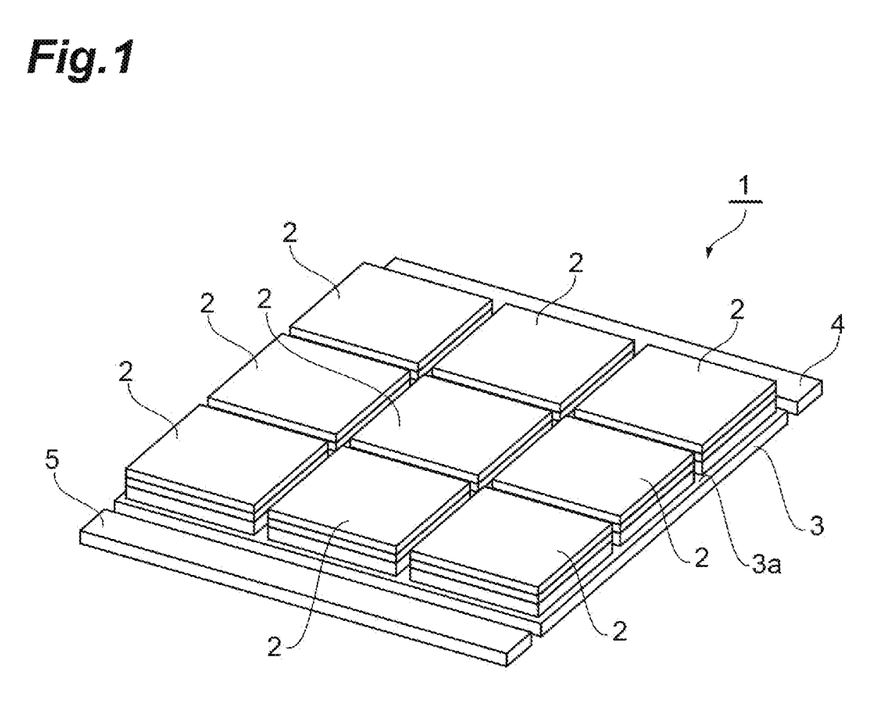
FIG. 1 is a perspective view showing a configuration of a radiation imaging apparatus according to an embodiment.

A radiation imaging apparatus 1 shown in FIG. 1 obtains a two-dimensional image based on radiation arriving from an inspection target. The radiation is, for example, gamma rays, X-rays, alpha rays, beta rays, and the like. The radiation imaging apparatus 1 includes a plurality of radiation detectors 2 and a circuit board 3. The radiation detectors 2 are mounted on a circuit main surface 3a of the circuit board 3. Each of the radiation detectors 2 outputs a pixel signal corresponding to incident radiation. The radiation detector 2 includes a plurality of pixels G (refer to FIG. 4) and outputs a pixel signal for each of the pixels G. The pixel signal is used to generate a radiation image in an image generation part 4. The circuit board 3 receives the pixel signal output from the radiation detector 2. The circuit board 3 has a signal line for providing a control signal from a control part 5 to the radiation detector 2. Further, the circuit board 3 has a signal line for outputting a pixel signal to the image generation part 4. Further, the circuit board 3 may have a signal line for electrically connecting the radiation detectors 2 to each other.

Figure 2:
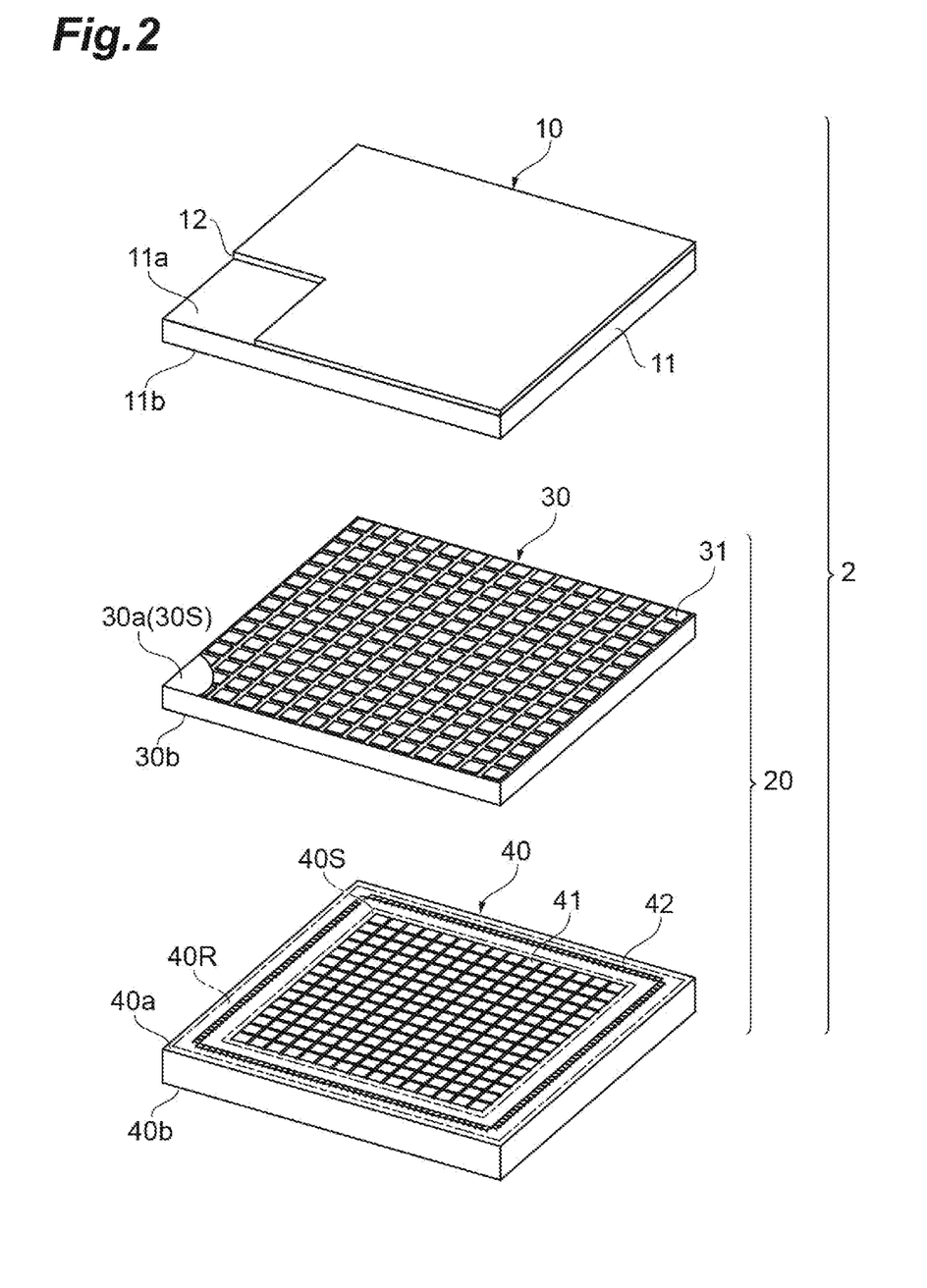
FIG. 2 is a perspective view of the radiation imaging apparatus shown in FIG. 1 when seen from a first viewpoint in a state in which the radiation imaging apparatus is disassembled.
Figure 3:
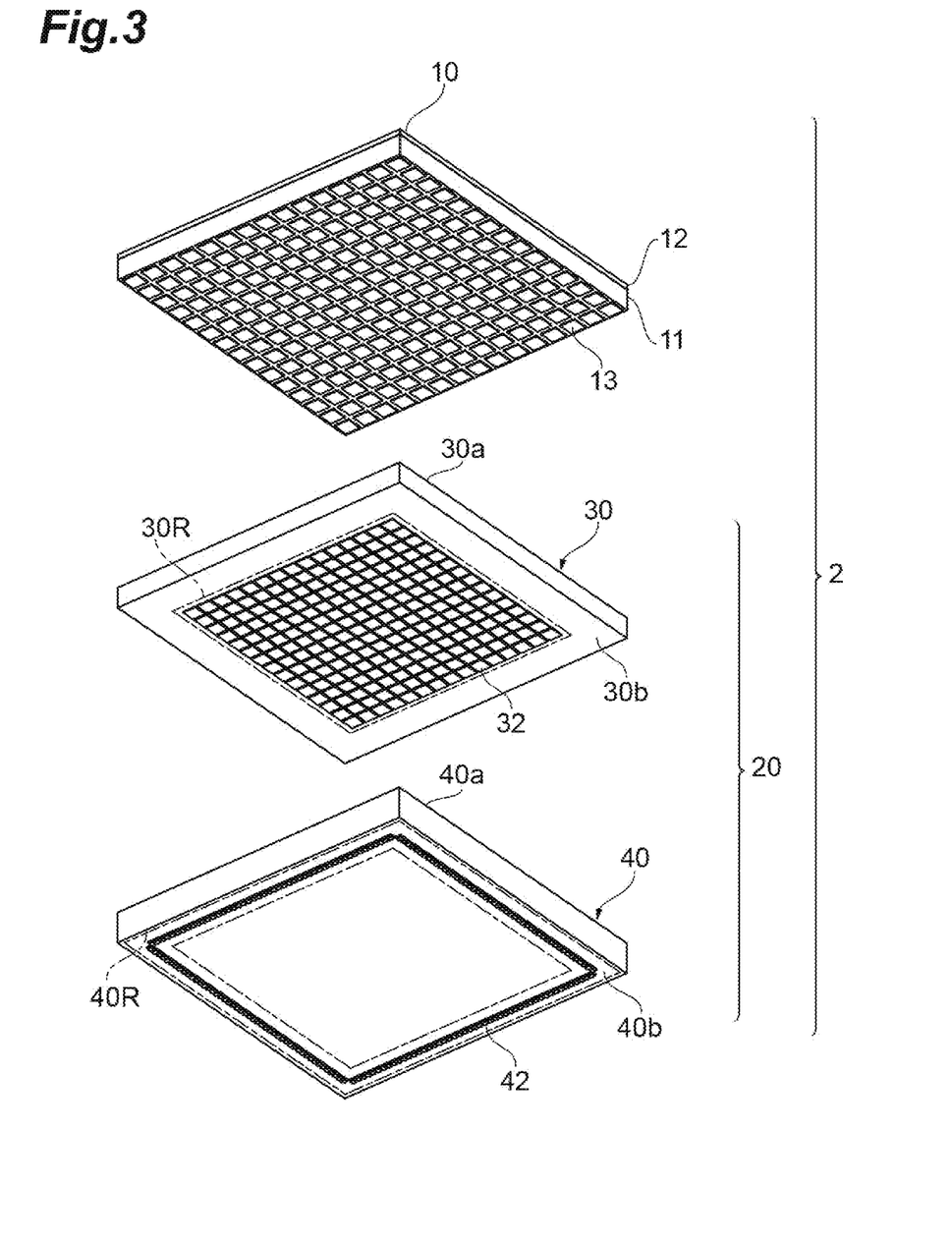
FIG. 3 is a perspective view of the radiation imaging apparatus shown in FIG. 1 when seen from a second viewpoint in the state in which the radiation imaging apparatus is disassembled.

As shown in FIGS. 2 and 3, the radiation detector 2 includes an electric charge generation part 10 and a reading part 20. Shapes of the electric charge generation part 10 and the reading part 20 are plate-shaped. The radiation detector 2 has a stacked structure. The electric charge generation part 10 is disposed on the reading part 20. The electric charge generation part 10 is electrically connected to the reading part 20. The electric charge generation part 10 generates an electric charge according to the incident radiation. The electric charge generation part 10 outputs the electric charge to the reading part 20. The reading part 20 generates a pixel signal using the electric charge generated by the electric charge generation part 10.

The electric charge generation part 10 includes a semiconductor detection part 11, a control electrode part 12, and an electric charge output electrode 13.

The semiconductor detection part 11 generates electron-hole pairs (electric charge pairs) due to the received X-rays. That is, the semiconductor detection part 11 converts the received radiation into a current signal (an electric charge signal) corresponding to energy thereof. A planar shape of the semiconductor detection part 11 is rectangular. A size of the semiconductor detection part 11 is, for example, about 9.6 mm×9.6 mm. The semiconductor detection part 11 has a semiconductor incident surface 11a that receives radiation such as X-rays, and a semiconductor output surface 11b that outputs an electric charge. A signal based on the electric charge is provided from the semiconductor output surface 11b to the reading part 20. As the semiconductor detection part 11, for example, a Cd(Zn)Te electric charge generator, a Si electric charge generator, a Ge electric charge generator, a GaAs electric charge generator, a GaN electric charge generator, a T1Br electric charge generator, or the like may be used. Further, a device including a scintillator and a photodetector may be used as the semiconductor detection part 11. The scintillator converts X-rays into light. The photodetector converts the light generated by the scintillator into an electric charge.

The control electrode part 12 is provided on the semiconductor incident surface 11a. The control electrode part 12 covers the entire surface of the semiconductor incident surface 11a. In a plan view, a planar shape of the control electrode part 12 coincides with the planar shape of the semiconductor incident surface 11a. The control electrode part 12 forms an electric field in a region in which the semiconductor detection part 11 is disposed. The electric field determines a direction in which the electric charge generated in the semiconductor detection part 11 moves. The control electrode part 12 generates the electric field inside the semiconductor detection part 11 so that the electric charge moves toward the semiconductor output surface 11b.

A plurality of electric charge output electrodes 13 are provided on the semiconductor output surface 11b. Each of the electric charge output electrodes 13 may be a bump. One electric charge output electrode 13 corresponds to one pixel G. Therefore, a region in which the electric charge output electrodes 13 are disposed is a pixel region. For example, when n electric charge output electrodes 13 are disposed on a first side and m electric charge output electrodes 13 are disposed on a second side, the total number of electric charge output electrodes 13 is k (k=n×m). In this case, it can be said that the number of pixels of one radiation detector 2 is k. Additionally, when the radiation imaging apparatus 1 has p radiation detectors 2, it can be said that the number of pixels of the radiation imaging apparatus 1 is r (r=k×p).

The number of pixels of one radiation detector 2 is, for example, 96. Therefore, the number of electric charge output electrodes 13 is also 96. As described above, assuming that the size of the semiconductor detection part 11 is a square of about 9.6 mm×9.6 mm, a distance between the electric charge output electrodes 13 is 100 μm. In FIG. 2 and the like, for convenience of illustration, the number of electric charge output electrodes 13 is shown as a number less than 96.

The reading part 20 generates a pixel signal based on the electric charge generated by the semiconductor detection part 11. The pixel signal is a digital value. The reading part 20 outputs the pixel signal to the circuit board 3. The reading part 20 includes an intermediate substrate 30 and a lead-out substrate 40.

An intermediate substrate 30 guides the electric charge generated by the semiconductor detection part 11 to a lead-out substrate 40. Although the details will be described later, the arrangement of the electric charge output electrode 13 is different from the arrangement of a first lead-out electrode 41. Therefore, the intermediate substrate 30 functions to connect the electrodes disposed at different positions from each other. This function is called pitch conversion. Therefore, the intermediate substrate 30 is a pitch conversion substrate. The intermediate substrate 30 converts a pitch of the electric charge output electrode 13 of the semiconductor detection part 11 into a pitch of the first lead-out electrode 41 of the lead-out substrate 40.

The intermediate substrate 30 has an intermediate input surface 30a and an intermediate output surface 30b. The intermediate input surface 30a faces the electric charge generation part 10. The intermediate output surface 30b faces the lead-out substrate 40.

The intermediate input surface 30a faces the semiconductor output surface 11b of the semiconductor detection part 11. A rectangular intermediate input region 30S is set on the intermediate input surface 30a in a plan view. The intermediate input region 30S is set over almost the entire surface of the intermediate input surface 30a. For example, the intermediate input region 30S may be the entire surface of the intermediate input surface 30a. In the intermediate input region 30S, a plurality of first intermediate electrodes 31 are disposed two-dimensionally at equal intervals. The electric charge output electrode 13 of the semiconductor detection part 11 is electrically connected to the first intermediate electrode 31. Therefore, a pitch of the first intermediate electrodes 31 adjacent to each other is the same as a pitch of the electric charge output electrodes 13. For example, when the pitch of the electric charge output electrodes 13 is 100 μm, the pitch of the first intermediate electrodes 31 is also 100 μm. On the intermediate input surface 30a, the intermediate input region 30S corresponds to the pixel region.

A rectangular intermediate output region 30R is set on the intermediate output surface 30b in a plan view. In a plan view, the entire intermediate output region 30R overlaps the intermediate input region 30S. That is, an area of the intermediate output region 30R is smaller than an area of the intermediate input region 30S. A plurality of second intermediate electrodes 32 (second electrodes) are disposed two-dimensionally in the intermediate output region 30R.

The first intermediate electrodes 31 (refer to FIG. 2) are disposed in the vicinity of a side surface of the intermediate substrate 30. On the other hand, the second intermediate electrodes 32 (refer to FIG. 3) are not disposed in the vicinity of the side surface of the intermediate substrate 30. The second intermediate electrode 32 disposed on the outermost circumference is separated from the side surface of the intermediate substrate 30. A distance from the second intermediate electrode 32 to the side surface of the intermediate substrate 30 is larger than a distance from the first intermediate electrode 31 to the side surface of the intermediate substrate 30. For example, the distance from the second intermediate electrode 32 to the side surface of the intermediate substrate 30 is larger than a length of several second intermediate electrodes 32. This distance corresponds to a width of a lead-out output part 40R which will be described later. Assuming that the width of the lead-out output part 40R is 200 µm, the distance from the second intermediate electrode 32 to the side surface of the intermediate substrate 30 is also approximately 200 µm.

Figure 4:
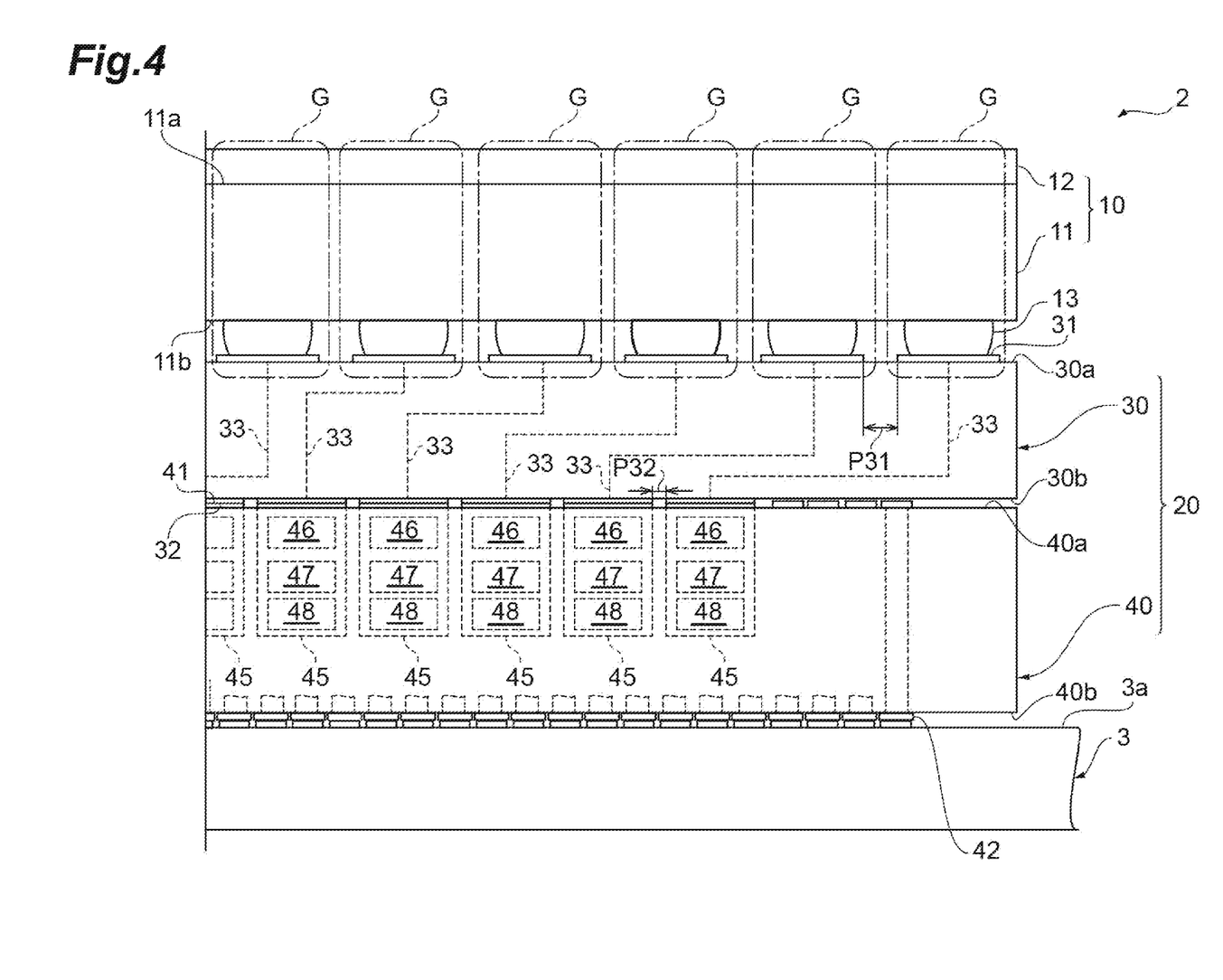
FIG. 4 is an enlarged view showing a radiation detector included in the radiation imaging apparatus of FIG. 1.

As shown in FIG. 4, one first intermediate electrode 31 is electrically connected to one second intermediate electrode 32. Therefore, the intermediate substrate 30 has a wiring 33 that connects the first intermediate electrode 31 to the second intermediate electrode 32. A configuration of the wiring 33 is not particularly limited. For example, the wiring 33 may be a combination of a portion that extends in a thickness direction of the intermediate substrate 30 and a portion that extends in a direction of a surface of the intermediate substrate 30. Further, the wiring 33 may extend linearly from the first intermediate electrode 31 to the second intermediate electrode 32. Such a wiring structure is referred to as a diagonal via. According to the diagonal via, a pitch conversion distance that is a wiring distance from the first intermediate electrode 31 to the second intermediate electrode 32 can be shortened. As a result, the influence of stray capacitance can be reduced.

The number of the first intermediate electrodes 31 is the same as the number of the second intermediate electrodes 32. A pitch P32 of the second intermediate electrodes 32 adjacent to each other is smaller than a pitch P31 of the first intermediate electrodes 31 adjacent to each other. Assuming that the pitch P31 of the first intermediate electrode 31 is 100 µm, 80 µm can be exemplified as the pitch P32 of the second intermediate electrode 32. In the present embodiment, the plurality of second intermediate electrodes 32 are disposed at equal intervals, but the pitch P32 of the second intermediate electrodes 32 is not limited to the equal intervals.

Referring to FIGS. 2 and 3 again, the lead-out substrate 40 receives an electric charge and generates a pixel signal corresponding to the received electric charge. The lead-out substrate 40 has a lead-out input surface 40a and a lead-out output surface 40b. The lead-out input surface 40a faces the intermediate output surface 30b. The lead-out output surface 40b faces the circuit board 3. Further, the lead-out substrate 40 includes a lead-out input part 40S, a lead-out output part 40R, and a plurality of signal processing parts 45 (refer to FIG. 4).

The lead-out input part 40S is formed on the lead-out input surface 40a. The lead-out input part 40S includes a plurality of first lead-out electrodes 41. The arrangement of the first lead-out electrodes 41 corresponds to the arrangement of the second intermediate electrodes 32. That is, the first lead-out electrodes 41 face the second intermediate electrodes 32. As a result, one first lead-out electrode 41 is electrically connected to one second intermediate electrode 32. Then, the first lead-out electrode 41 receives an electric charge from the second intermediate electrode 32.

The lead-out output part 40R functions as a signal input and output part between the radiation detector 2 and another component (the the control part 5 and the image generation part 4). For example, the lead-out output part 40R receives a control signal from the control part 5. Further, the lead-out output part 40R outputs a digital value to the image generation part 4. The lead-out output part 40R is formed to surround the lead-out input part 40S. For example, a width of the lead-out output part 40R is 200 µm. In a plan view, the lead-out output part 40R has a frame shape.

The lead-out output part 40R includes a plurality of second lead-out electrodes 42. For example, in the frame-shaped lead-out output part 40R, 50 second lead-out electrodes 42 are disposed on one side. Therefore, 200 second lead-out electrodes 42 are disposed on the four sides constituting the lead-out output part 40R. One second lead-out electrode 42 is connected to one signal processing part 45. The second lead-out electrode 42 surrounds the lead-out input part 40S. In other words, the plurality of second lead-out electrodes 42 are disposed on the lead-out input surface 40a to surround the plurality of first lead-out electrodes 41. Each of the second lead-out electrode 42 is a through electrode. That is, the second lead-out electrode 42 reaches from the lead-out input surface 40a to the lead-out output surface 40b. Each of the second lead-out electrodes 42 is electrically connected to the circuit board 3 via a bump provided on the lead-out output surface 40b.

As shown in FIG. 4, the signal processing part 45 converts an electric charge into a pixel signal which is the digital value. One signal processing part 45 is connected to one first lead-out electrode 41. That is, one signal processing part 45 is connected to one pixel G. Therefore, the reading part 20 includes a plurality of signal processing parts 45. The signal processing part 45 receives an electric charge from the lead-out input part 40S. The signal processing part 45 outputs a digital value from the lead-out output part 40R. More specifically, the signal processing part 45 converts the charge output by the electric charge generation part 10 into an energy integration signal which is a pixel signal. The energy integration signal includes at least information on the energy possessed by the incident radiation.

Figure 5:
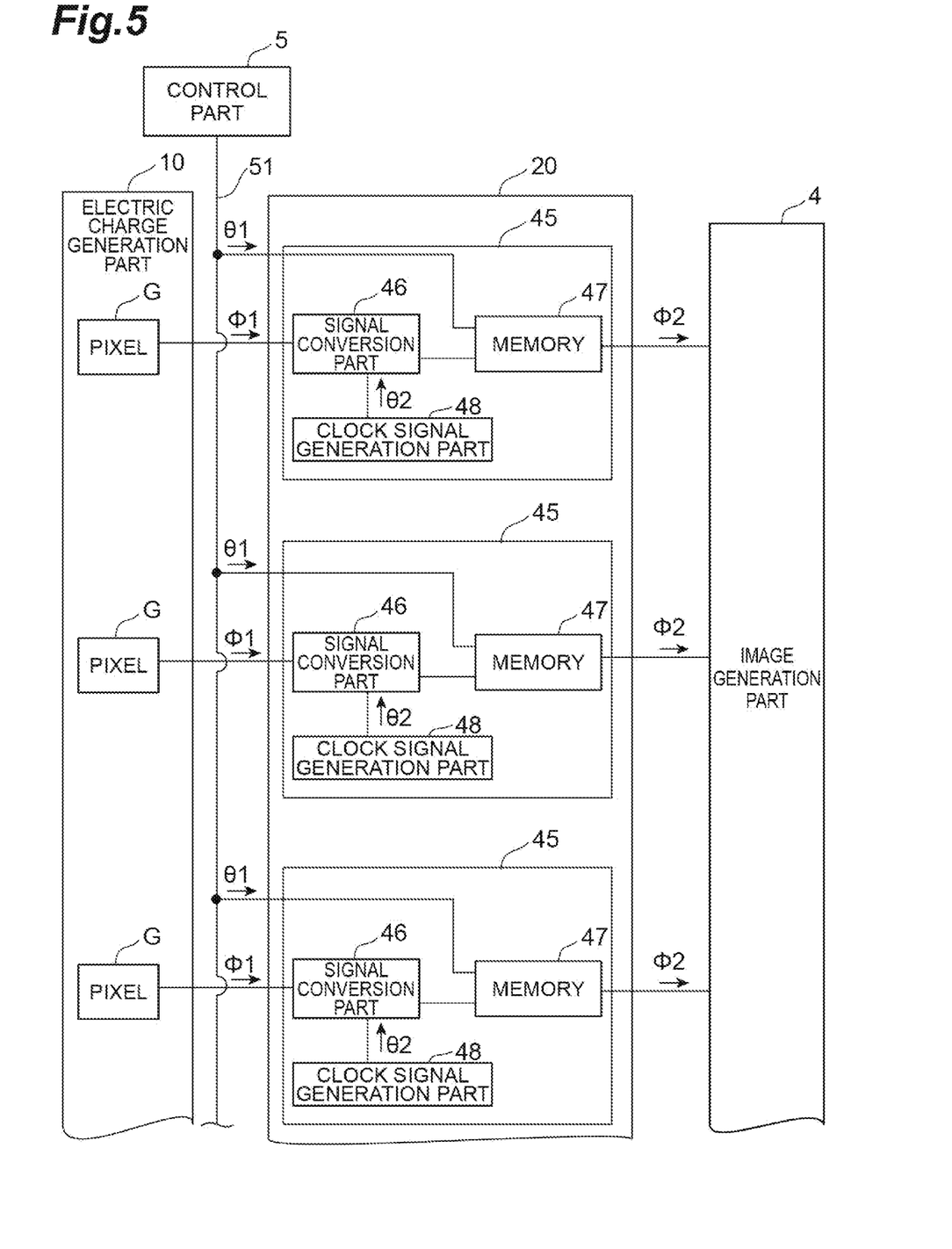
FIG. 5 is a block diagram showing a configuration of a signal processing part included in the radiation imaging apparatus shown in FIG. 4.

As shown in FIG. 5, the signal processing part 45 includes a signal conversion part 46, a memory 47, and a clock signal generation part 48. Since the signal processing part 45 is connected for each of the pixels G, the number of signal processing parts 45 is the same as the number of pixels G. Similarly, the number of signal conversion parts 46 is the same as the number of pixels G, the number of memories 47 is the same as the number of pixels G, and the number of clock signal generation parts 48 is also the same as the number of pixels G. That is, one signal conversion part 46, one memory 47, and one clock signal generation part 48 are connected to one pixel G.

The signal conversion part 46 is connected to the electric charge output electrode 13 of the electric charge generation part 10 via the wiring 33 of the intermediate substrate 30. The signal conversion part 46 receives an electric charge $\varphi 1$ from the electric charge generation part 10. The signal conversion part 46 discretizes an analog signal based on the electric charge $\varphi 1$. The analog signal is expressed as a voltage. The voltage corresponds to the energy of radiation or the number of particles incident on the corresponding pixel G of the electric charge generation part 10. Therefore, the signal conversion part 46 is an A/D converter that outputs a digital signal. For example, a resolution of the signal conversion part 46 may be 10 bits.

The signal conversion part 46 is operated by a clock signal θ2 provided by the clock signal generation part 48. When the signal conversion part 46 receives the clock signal θ2, the signal conversion part 46 performs an operation of transmitting an analog signal generated due to the incidence of radiation from the pixel G, an operation of resetting the electric charge accumulated in the pixel G, and an operation of converting the transmitted analog signal into a digital signal. In addition to the above-described operations, the signal conversion part 46 may perform other desired operations.

The clock signal generation part 48 generates the clock signal θ2 necessary for the operation of the signal conversion part 46. Then, the clock signal generation part 48 provides the clock signal θ2 to the signal conversion part 46. That is, one clock signal generation part 48 is connected to one signal conversion part 46. In other words, an output destination of a certain clock signal generation part 48 is one specified signal conversion part 46. The signal conversion part 46 is provided for each of the pixels G. Therefore, it can be said that the clock signal generation part 48 is also provided for each of the pixels G. With such a configuration, the clock signal generation part 48 may be disposed to be adjacent to the signal conversion part 46. As a result, a length of a signal line from the clock signal generation part 48 to the signal conversion part 46 can be shortened. When the signal line is shortened, a transmission distance of the clock signal θ2 is also shortened, and thus signal delay is less likely to occur. Further, a frequency of the clock signal can be increased to about 100 MHz.

Figure 6:
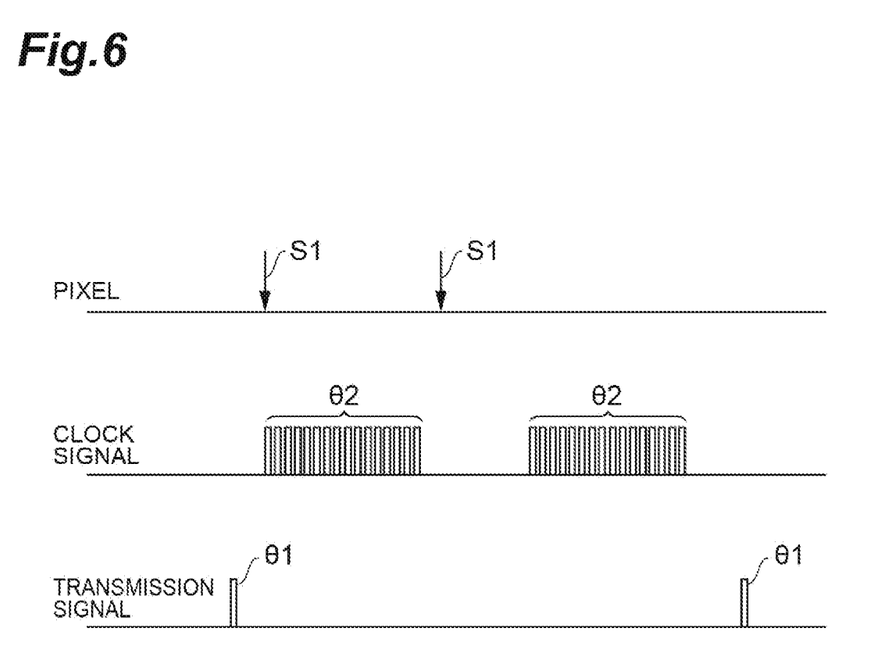
FIG. 6 is a diagram for describing an operation of the radiation imaging apparatus.

The clock signal generation part 48 starts generation of the clock signal θ2 triggered by the incidence of radiation on the corresponding pixel G (refer to a reference numeral S1 in FIG. 6). The clock signal generation part 48 outputs a predetermined number of pulses in accordance with the trigger. The number of output pulses may be the number required for an analog-to-digital conversion operation in the signal conversion part 46. For example, when one incidence of radiation is detected, the clock signal generation part 48 outputs 16 pulses as the clock signal θ2.

Since the clock signal generation part 48 is provided for each of the pixels G, the operations related to each of the pixels G can be made independent. In other words, it is not necessary to synchronize the operations of the plurality of signal conversion parts 46. Therefore, a signal for synchronizing the operations of the plurality of signal conversion parts 46 is also unnecessary. For example, when radiation is incident on a certain pixel G, the signal conversion part 46 can immediately start an operation of generating a digital signal. That is, it can be said that the operation of the signal conversion part 46 is synchronized with the incidence of radiation. According to such an operation, since a signal conversion process is performed immediately after the radiation is incident, a problem of phase shift does not occur. In addition, no unnecessary waiting time is generated. Such an operation has a high affinity for a photon counting type detector that performs the signal conversion process for each randomly incident particle.

Further, even when radiation is incident on the plurality of pixels G at a certain timing, the operation of independently generating the digital signals can be started. Further, it is also possible to operate only the signal conversion part 46 corresponding to the pixel G on which the radiation is incident, and not to operate the signal conversion part 46 corresponding to the pixel G on which the radiation is not incident. When the signal conversion operation is uniformly performed for all the pixels G, the power consumption increases in proportion to the number of pixels as the number of pixels increases. However, since the radiation imaging apparatus 1 of the present embodiment can operate only the necessary signal conversion part 46, the power consumption is not proportional to the number of pixels. Therefore, it is possible to achieve both an increase in the number of pixels and suppression of an increase in the power consumption.

The memory 47 is connected to the signal conversion part 46. The memory 47 receives a digital signal φ2 from the signal conversion part 46. Then, the memory 47 stores the digital signal φ2 each time when the digital signal (φ2 is input. The memory 47 sequentially stores the digital signal (φ2 in a predetermined memory space. The memory 47 is connected to the control part 5 via a wiring 51 (a wiring part). An input of the wiring 51 is one, and an output of the wiring 51 is a plurality. Additionally, the input of the wiring 51 is connected to the control part 5, and the output of the wiring 51 is connected to the memory 47 of the signal processing part 45. That is, a transmission signal θ1 is output from one control part 5 to the plurality of memories 47. The control part 5 that outputs the transmission signal θ1 has a function as a transmission signal generation part.

The memory 47 outputs a digital signal φ2 to the image generation part 4 in accordance with the transmission signal θ1 provided by the control part 5. That is, since the memory 47 does not receive the clock signal θ2, it is not controlled by the clock signal θ2. In other words, the operation of the signal conversion part 46 and the operation of the memory 47 are based on signals different from each other. Therefore, each of the operations is also independent of each other.

The radiation imaging apparatus 1 includes the plurality of pixels G that generate an electric charge corresponding to energy or the number of particles of the incident radiation, the plurality of signal processing parts 45 that are respectively connected to the plurality of pixels G and generate a digital value based on the electric charge provided by each of the pixels G, and the circuit board 3 in which a radiation detector 2 including the plurality of pixels G and the plurality of signal processing parts 45 is disposed in a two-dimensional manner. Each of the plurality of signal processing parts 45 includes the signal conversion part 46 that converts an analog value based on the electric charge into a digital value, and the clock signal generation part 48 that provides a clock signal for generating a digital value to the signal conversion part.

In the radiation imaging apparatus 1, the signal processing part 45 is provided for each of the pixels G. The signal processing part 45 includes the signal conversion part 46 and the clock signal generation part 48. That is, in the radiation imaging apparatus 1, the clock signal generation part 48 is provided for each of the pixels G. With such a configuration, it is possible to drive only the signal conversion part 46 corresponding to the pixel G on which the radiation is incident, and not to drive the signal conversion part 46 corresponding to the pixel G on which the radiation is not incident. Therefore, even when the number of pixels G increases, the signal conversion part 46 which does not need to be operated is not operated, and thus an increase in the power consumption can be suppressed.

The radiation imaging apparatus 1 of the present invention is not limited to the above-described embodiment.

REFERENCE SIGNS LIST

1 . . . Radiation imaging apparatus, 2 . . . Radiation detector, 3 . . . Circuit board, 4 . . . Image generation part, 5 . . . Control part, 10 . . . Electric charge generation part, 20 . . . Reading part, 11 . . . Semiconductor detection part, 12 . . . Control electrode part, 13 . . . Electric charge output electrode, 11$a$ . . . Semiconductor incident surface, 11$b$ . . . Semiconductor output surface, 30 . . . Intermediate substrate, 40 . . . Lead-out substrate, 30$a$ . . . Intermediate input surface (first main surface), 30$b$ . . . Intermediate output surface (second main surface), 30S . . . Intermediate input region, 31 . . . First intermediate electrode (first electrode), 30R . . . Intermediate output region, 32 . . . Second intermediate electrode (second electrode), 40$a$ . . . Lead-out input surface, 40$b$ . . . Lead-out output surface, 41 . . . First lead-out electrode, 42 . . . Second lead-out electrode, 45 . . . Signal processing part, 46 . . . Signal conversion part, 47 . . . Memory, 48 . . . Clock signal generation part.

The invention claimed is:

1. A radiation imaging apparatus comprising:
   a plurality of pixels configured to generate an electric charge corresponding to energy or the number of particles of incident radiation;
   a plurality of signal processing parts respectively connected to the plurality of pixels and configured to generate a digital value based on the electric charge provided by each of the pixels; and
   a circuit board in which a radiation detector including the plurality of pixels and the plurality of signal processing parts is disposed in a two-dimensional manner,
   wherein each of the plurality of signal processing parts includes a signal conversion part configured to convert an analog value based on the electric charge into the digital value, and a clock signal generation part configured to provide the signal conversion part with a clock signal to convert the analog value based on the electric charge into the digital value.

2. The radiation imaging apparatus according to claim 1, wherein the clock signal generation part starts an operation of providing the clock signal to the signal conversion part triggered by generation of the electric charge due to incidence of the radiation on the pixels, and wherein a number of output pulses of the clock signal is a predetermined number required for a conversion operation of the signal conversion part.

3. The radiation imaging apparatus according to claim 1, further comprising:
   a transmission signal generation part configured to provide a transmission signal for outputting the digital value from the signal processing part to the circuit board to each of the plurality of signal processing parts; and
   a wiring unit configured to transmit the transmission signal to the signal processing part.

4. The radiation imaging apparatus according to claim 2, further comprising:
   a transmission signal generation part configured to provide a transmission signal for outputting the digital value from the signal processing part to the circuit board to each of the plurality of signal processing parts; and
   a wiring unit configured to transmit the transmission signal to the signal processing part.

* * * * *